US010441508B2

United States Patent
Bengard

(10) Patent No.: US 10,441,508 B2
(45) Date of Patent: Oct. 15, 2019

(54) SYSTEMS AND METHODS FOR HIGH HUMIDITY CURING WITHIN TABLET COATING SYSTEM

(71) Applicant: Mallinckrodt LLC, Hazelwood, MO (US)

(72) Inventor: Greg Bengard, Hazelwood, MO (US)

(73) Assignee: SPECGX LLC, Webster Groves, MO (US)

( * ) Notice: Subject to any disclaimer, the term of this patent is extended or adjusted under 35 U.S.C. 154(b) by 0 days.

(21) Appl. No.: 15/568,587

(22) PCT Filed: Apr. 24, 2015

(86) PCT No.: PCT/US2015/027558
§ 371 (c)(1),
(2) Date: Oct. 23, 2017

(87) PCT Pub. No.: WO2016/171723
PCT Pub. Date: Oct. 27, 2016

(65) Prior Publication Data
US 2018/0104151 A1    Apr. 19, 2018

(51) Int. Cl.
*A61J 3/00* (2006.01)
*A61K 9/28* (2006.01)
(Continued)

(52) U.S. Cl.
CPC .............. *A61J 3/005* (2013.01); *A61K 9/2893* (2013.01); *B05B 12/12* (2013.01); *B05B 16/60* (2018.02); *B05D 3/0486* (2013.01); *F24F 6/18* (2013.01); *F24F 13/04* (2013.01); *F24F 13/08* (2013.01); *A61J 3/06* (2013.01); *B05B 13/0257* (2013.01)

(58) Field of Classification Search
CPC ...... A23G 3/26; A23G 3/0063; A23G 3/0095; A23G 3/2076; A61J 3/005; A61J 3/06; F24F 13/08; F24F 13/04; F24F 6/18; F24F 13/085; F24F 13/28; F24F 13/222; F24F 2013/227; B30B 11/34; B05B 12/12; B05B 16/60; B05B 13/0257; B05D 3/0486; B05D 3/0254; B05D 2401/20; B05C 3/08; B05C 15/00; A23L 5/21; A61K 9/2893;
(Continued)

(56) References Cited

U.S. PATENT DOCUMENTS 3,448,718 A    6/1969  Green et al.
4,860,461 A *  8/1989  Tamaki ................. A23N 12/10
                                                    34/68
(Continued)

FOREIGN PATENT DOCUMENTS

WO    WO2014/104070    *  7/2014

OTHER PUBLICATIONS

International Search Report for PCT/US2015/027558 dated Jul. 29, 2015, 3 pages.

*Primary Examiner* — Laura Edwards

(57) ABSTRACT

The disclosure encompasses systems and methods for performing high temperature and high humidity curing of tablets using air flow delivered from a recirculating air handler to a pan coater of a tablet coating device. The recirculating air handler may be integrated into a preexisting tablet coating device so that the air flow may be delivered by the preexisting air handler or by the recirculating air handler as desired.

14 Claims, 11 Drawing Sheets

(51) Int. Cl.
*B05D 3/04* (2006.01)
*F24F 6/18* (2006.01)
*F24F 13/04* (2006.01)
*F24F 13/08* (2006.01)
*A61J 3/06* (2006.01)
*B05B 16/60* (2018.01)
*B05B 12/12* (2006.01)
*B05B 13/02* (2006.01)

(58) Field of Classification Search
CPC .... A61K 9/28; A24B 3/02; A24B 3/04; F26B 21/08; F26B 21/10; F26B 21/086
USPC ........ 118/17, 19, 20, 418; 34/448, 449, 469, 34/470, 471, 474, 475, 476, 72, 218, 219, 34/235, 446, 468, 477, 77, 78; 427/2.18; 426/297, 302–310
See application file for complete search history.

(56) References Cited

U.S. PATENT DOCUMENTS

| | | | |
|---|---|---|---|
| 4,984,587 A * | 1/1991 | Neville | A24B 3/04 131/302 |
| 2013/0023196 A1 | 1/2013 | Fisher | |
| 2014/0017310 A1 | 1/2014 | Gower et al. | |
| 2016/0037792 A1 * | 2/2016 | Kusaura | A23F 5/16 426/460 |

* cited by examiner

SYSTEMS AND METHODS FOR HIGH HUMIDITY CURING WITHIN TABLET COATING SYSTEM

CROSS-REFERENCE TO RELATED APPLICATION

This application claims priority from PCT application No. PCT/US2015/027558 filed on Apr. 24, 2015 which is hereby incorporated by reference in its entirety.

BACKGROUND OF THE INVENTION

The formulations of a variety of active pharmaceutical compounds make use of a wide range of polymer coatings such as enteric coatings and other release-modifying coatings to produce a formulation with a desired release profile. These coating materials, which are typically polymer compositions, may be applied as one or more film coatings over a core tablet under controlled conditions to produce a modified-release formulation that may include the tablet covered with one or more layers of different polymer compositions.

Existing tablet coating systems typically include a pan coater used to apply the film coatings to tablet cores to form pharmaceutical compositions. The pan coater may include a coating pan or perforated rotating drum that rotates within the controlled environment inside a cabinet. Within the cabinet, a spraying system may pump a fine mist of coating solution toward tablets within the coating pan under controlled conditions to form a thin film coating on the tablets. The controlled conditions within the cabinet containing the coating pan result in the solvent portion of the coating solution to rapidly evaporate upon contact with the surface of the tablets, leaving behind the solids portion of the coating solution to form the coating.

The properties of the coated tablets are highly sensitive to variations in the operational parameters of the spraying system as well as the controlled conditions within the cabinet. Typically, the controlled conditions within the cabinet include elevated temperature and low humidity to facilitate the rapid evaporation of the coating solution. To this end, an air handling unit may deliver heated and dehumidified air into the cabinet, where it passes over the tablets within the coating pan and subsequently exhausts out a separate exhaust. This one-way airflow provides a low-humidity heated airflow to dry the tablets, and also transports unused coating solution out of the coating pan via the exhaust flow to provide additional control over the coating process.

To complete the production of coated tablet compositions, the coated tablets may be subjected to an additional curing process to allow the polymer coating to fully cure into a particular form to impart the desired coating properties, such as coating smoothness or pH-dependent solubility. In some cases, the curing process may include exposing the coated tablets to a particular temperature profile for a predetermined time period. In these cases, the additional curing process may be performed within the pan coater. However, for certain polymer materials, the curing process may require process conditions that extend beyond the capabilities of existing pan coaters.

One type of tablet formulation may include ingredients that require an additional curing process conducted at relatively high humidity to impart the desired coating properties. High humidity conditions are at odds with typical tablet coating conditions. In fact, many defects in tablet coating processes, such as picking, sticking, erosion, peeling, and/or frosting are attributed to inadequate drying of the coated tablets, which may in part be attributed to humid coating conditions. Thus, in order to perform a high humidity curing process, coated tablets may be removed to a separate curing chamber for exposure to high humidity as needed. However, transferring the uncured coated tablets to a separate curing chamber may impact tablet quality by exposing the tablets to undesired temperature, humidity and/or mechanical damage during transfer. In addition, the transfer to a separate curing chamber may add additional time and cost to the manufacturing process.

A need exists in the art for a process and method of providing high humidity conditions within an existing pan coater device. Such a process and method may also enhance the quality, production time and production costs of tablet coatings cured at high humidity conditions.

SUMMARY OF THE INVENTION

In one aspect a recirculating air handler for supplying high humidity air flow to a pan coater of a tablet coating system is provided. The recycling air handler includes: a humidifier to introduce moisture into the air flow in an amount resulting in a relative humidity in the air flow of up to about 90%; and a vent to release air from the recirculating air handler to the atmosphere via a vent valve. The vent valve may be opened as needed to maintain the pressure within the pan coater to at least 0.15 inches of water column below atmospheric pressure. The recirculating air handler may further include at least one inlet filter situated upstream of the humidifier to remove particulate matter from an airflow entering the recirculating air handler and at least one exit filter situated downstream of the of the humidifier to remove particulate matter from an airflow exiting the pan coater. The recirculating air handler may further include at least one drain pan. The at least one drain pan may include one or more of: an inlet drain pan situated upstream of the humidifier and at least one filter to remove any condensation formed out of the exhaust air delivered from the pan coater; and an outlet drain pan to remove any condensation formed out of the exit air to be delivered to the pan coater. The outlet drain pan may be situated downstream of the humidifier and a portion of the outlet drain pan may extend upstream of the humidifier. The recirculating air handler may further include: a supply air duct comprising a supply end operatively connected to supply air to the pan coater and an exit end opposite to the supply end and operatively connected to the exit of the recirculating air handler; and an exhaust duct comprising an exhaust end operatively connected to receive exhaust from the pan coater and an inlet end opposite to the exhaust end and operatively connected to the inlet of the recirculating air handler.

In another aspect, a tablet coating system to apply one or more coatings to a tablet is provided. The tablet coating system includes: a recirculating air handler to supply a humid air flow to a pan coater; a flow-through air handler to supply a low humidity air flow to the pan coater; and one or more ducts and one or more configurable valves. The recirculating air handler includes: a humidifier to introduce water vapor into the air flow in an amount resulting in a relative humidity in the air flow of up to about 90%; and a vent to release air from the recirculating air handler to the atmosphere via a vent valve. The vent valve is opened as needed to maintain an air pressure within the pan coater of at least 0.15 inches of water column below atmospheric pressure. The one or more configurable valves may be configured to: cut off flow through the recirculating air handler and direct the air flow from the flow-through air handler to a supply of the pan coater and from an exhaust of the pan coater to an exhaust stack; or cut off flow from the flow-through air handler and direct the air flow from an exit of the recirculating air handler to a supply of the pan coater and from the exhaust of the pan coater to an inlet of the flow-through air handler. The tablet coating system may also include at least one inlet filter situated upstream of the humidifier to remove particulate matter from an airflow entering the recirculating air handler and at least one exit filter situated downstream of the of the humidifier to remove particulate matter from an airflow exiting the recirculating air handler. The tablet coating system may further include at least one drain pan. The at least one drain pan may include one or more of: an inlet drain pan situated upstream of the humidifier and at least one filter to remove any condensation formed out of the exhaust air delivered from the pan coater; and an exit drain pan to remove any condensation formed out of the exit air to be delivered to the pan coater. The exit drain pan may be situated downstream of the humidifier and a portion of the exit drain pan may extend upstream of the humidifier. The one or more ducts may include: a supply duct that includes a supply end operatively connected to supply air to the pan coater and an exit end opposite to the supply end and operatively connected to the exit of the recirculating air handler; an exhaust duct comprising an exhaust end operatively connected to receive exhaust from the pan coater and an inlet end opposite to the exhaust end and operatively connected to the inlet of the recirculating air handler; an exhaust stack operatively connected to the exhaust duct between the exhaust end and the inlet end at one end and venting to the atmosphere at an opposite end; and a second supply duct operatively connected at a first end to an exit end of the flow-through air handler and operatively connected at a second end to the supply duct between the supply end and the exit end. The one or more valves may include: a first valve situated within the supply duct near the exit end; a second valve situated within the exhaust duct near the inlet end; a third valve situated within the exhaust stack; and a fourth valve situated within the second supply duct. The first and second valves may be opened and the third and fourth valve may be closed to supply the pan coater with humid air flow from the recirculating air handler; or the first and second valves may be closed and the third and fourth valves may be opened to supply the pan coater with low-humidity air flow from the flow-through air handler.

In an additional aspect, a method of supplying a humid air flow to a pan coater of a tablet coating system is provided. The method may include: establishing an air flow through a recirculating air handler operatively connected to receive exhaust air flow from the pan coater and to deliver a supply air flow to the pan coater; heating the air flow to pre-heat the pan coater, a supply duct delivering air flow to the pan coater, and an exhaust duct receiving exhaust flow from the pan coater; establishing and maintaining humid air flow within the pan coater for a duration of a humidification process; and clearing the humid air flow from pan coater. The air flow may be heated to a temperature ranging from about 50° c. to about 80° c. and a dew point ranging from about 45° c. to about 55° c. The humid air flow may be maintained at a humidity of up to about 90% relative humidity. The humid air flow may be produced by clean steam introduced into the flow from a humidifier situated within the recirculating air handler. The method may further include maintaining a pressure within the pan coater that is at least 0.15 inches of water column below atmospheric pressure. The pressure within the pan coater may be maintained by venting air flow from the recirculating air handler to the atmosphere as needed. The method may further include filtering particulate matter from the air flow received by the recirculating air handler by directing the airflow through one or more filters situated within the recirculating air handler. The humid air flow may be cleared from the pan coater by deactivating the humidifier and maintaining a pressure within the pan coater that is at least 0.25 inches of water column below atmospheric pressure. The method may further include reestablishing air flow through a flow-through air handler operatively connected to the supply duct and configured to receive external air from the atmosphere. Reestablishing air flow through the flow-through air handler may include blocking flow entering and exiting the recirculating air handler, opening flow from the flow-through air handler into the supply duct, and directing the exhaust flow from the pan coater through an exhaust stack into the atmosphere. The humid air flow may be provided to the pan coater with essentially no formation of condensation.

FIELD OF THE INVENTION

The disclosure encompasses systems and methods for performing high temperature and high humidity curing of tablets using a recirculating air handler integrated into a preexisting tablet coating system.

DESCRIPTION OF FIGURES

The following figures illustrate various aspects of the disclosure.

Other aspects and iterations of the invention are described in more detail below.

DETAILED DESCRIPTION OF THE INVENTION

It has been discovered that a tablet coating device may be modified to include a recirculating air handler capable of delivering relatively high temperature and high humidity air to the pan coater of the tablet coating device for use in one or more tablet curing processes with minimal impact on the pan coater's pre-existing capabilities. The recirculating air handler may be integrated into the duct and control systems of an existing tablet coating system and may be operated in a manner similar to the operation of the existing tablet coating system.

Figure 1:
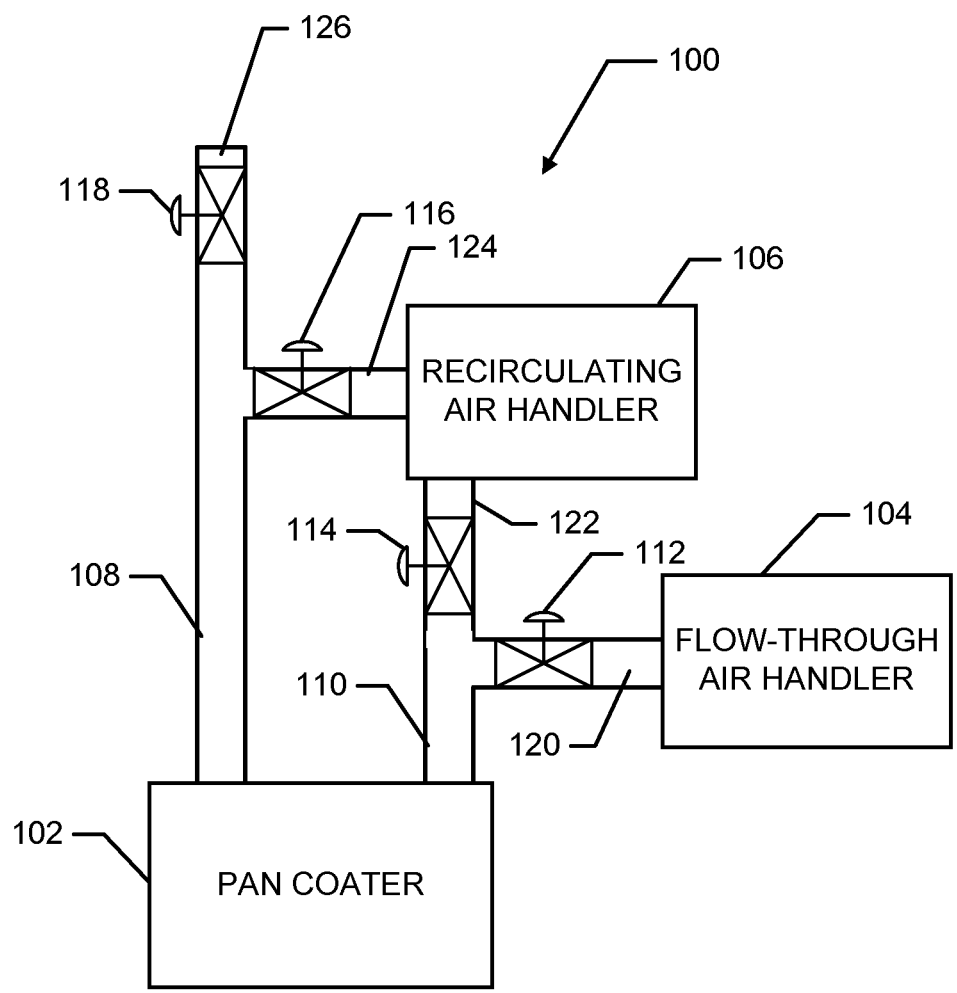
FIG. 1 is a block diagram illustrating the components of a tablet coating system modified with a recirculating air handler in one aspect.

FIG. 1 is a block diagram illustrating a tablet coating system 100 modified to incorporate a recirculating air handler 106. In this system 100, air is delivered to a pan coater 102 via a supply duct 110 and exits the pan coater 102 via an exhaust duct 108. The air delivered to the pan coater may be conditioned to a preselected temperature and humidity using either a flow-through air handler 104 or a recirculating air handler 106 depending on the desired process to be conducted within the pan coater 102. The selection of the flow-through air handler or the recirculating air handler for conditioning of the air introduced into the pan coater 102 may be implemented via valves 112, 114, 116, and 118 situated within the ducting of the system 100.

Any suitable fluid control device known in the art may be selected for use as a valve in the system 100. In one aspect, any known type of valve may be used including, but not limited to: a ball valve, a butterfly valve, a gate valve, a globe valve, a needle valve, and any other suitable valve types known in the art. In another aspect, a damper may be selected for use as a valve in the system 100 including, but not limited to: single blade dampers, multi-blade dampers, round dampers, louvers, and any other suitable type of damper known in the art.

Figure 2:
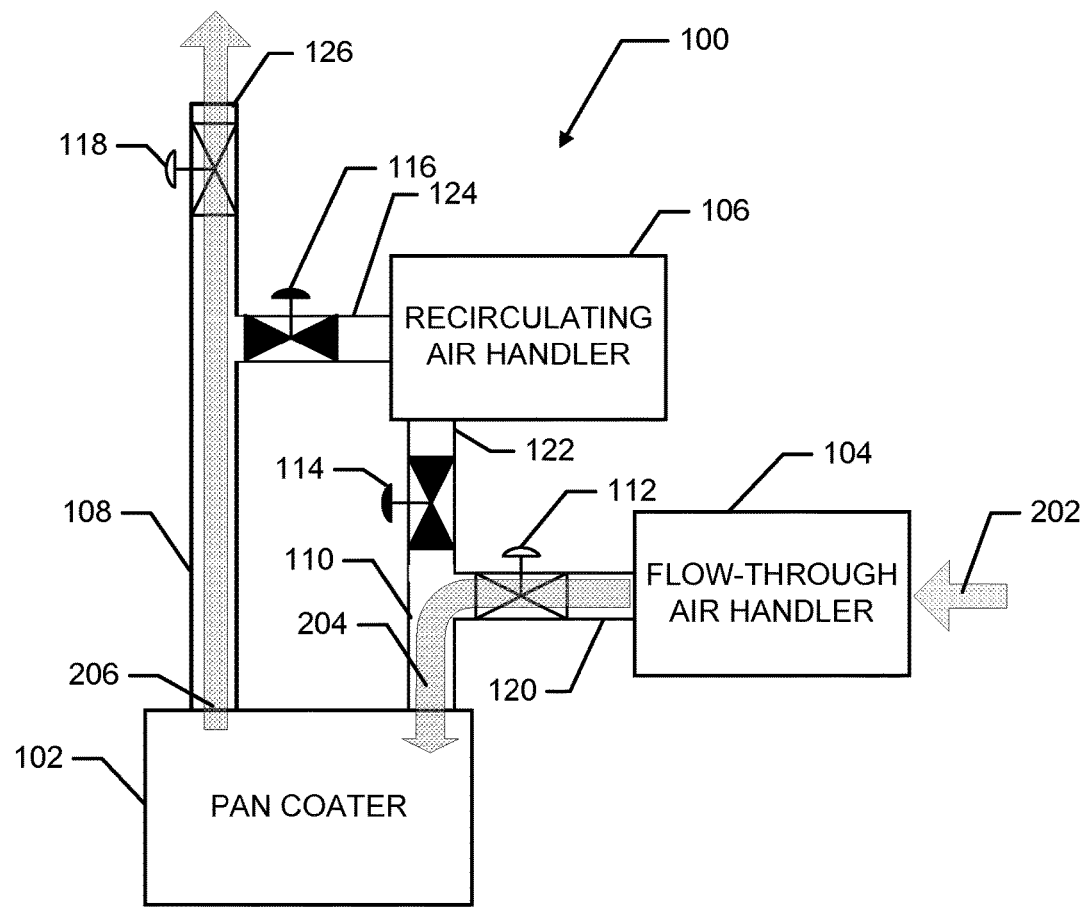
FIG. 2 is a block diagram illustrating the components of the modified tablet coating system of FIG. 1 operating in a preexisting mode in which the pan coater airflow is supplied by a flow-through air handler.

As illustrated in FIG. 2, to select the flow-through air handler for use in a preexisting mode of operation of the tablet coating system 100, valves 114 and 116 are closed and valves 112 and 118 are opened. Atmospheric air 202 enters the flow-through air handler 104 to be filtered, heated, and/or dehumidified as needed. The conditioned air 204 is directed to the pan coater 102 via the open valve 112 and is prevented from entering the recirculating air handler by the closed valve 114. After passing through the pan coater 102, the exhaust air 206 is directed out of the pan coater 102 and through the exhaust stack 126 through the open valve 118; the exhaust air is prevented from entering the recirculating air handler by the closed valve 116. In this preexisting mode, the tablet coating system 100 may operate with all the capabilities of the preexisting system including, but not limited to: preheating tablets, applying one or more coatings to the tablets, and drying the tablets.

Figure 3:
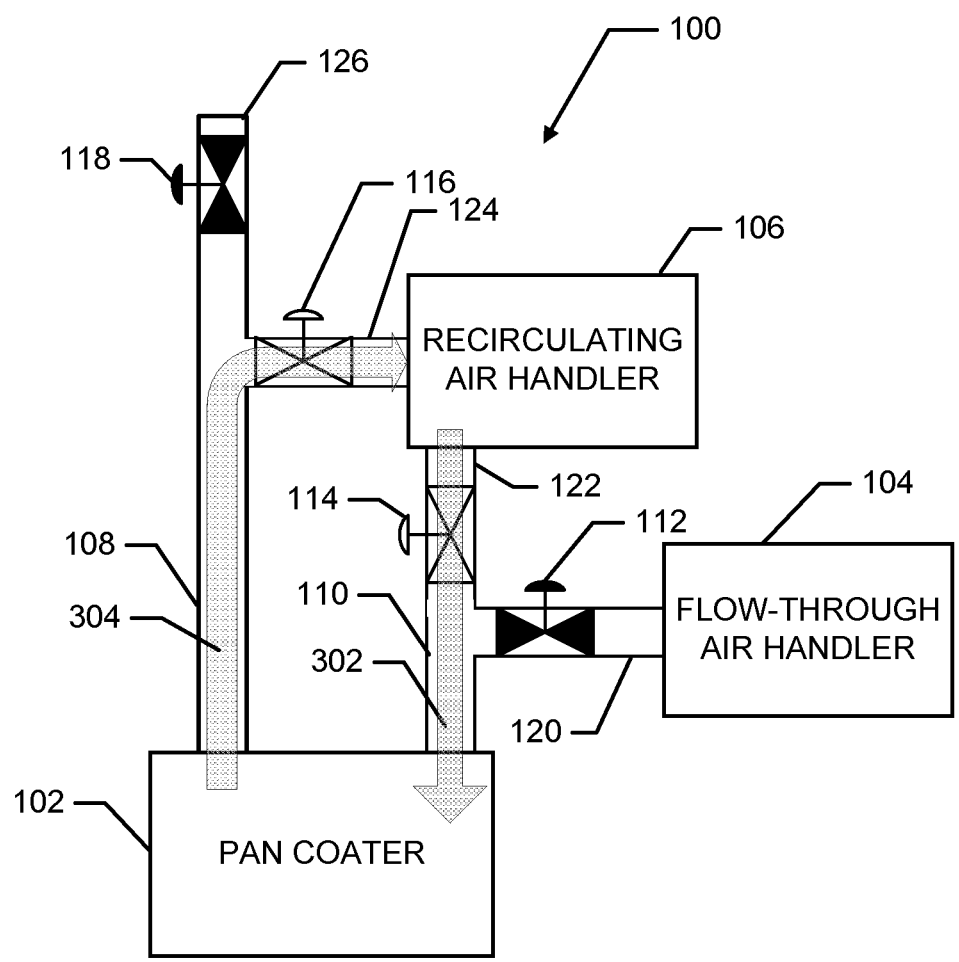
FIG. 3 is a block diagram illustrating the components of the modified tablet coating system of FIG. 1 operating in a humidification mode in which the pan coater airflow is supplied by the recirculating air handler.

The recirculating air handler 106 may be selected for use in a humidification mode by closing valves 112 and 118 and opening valves 114 and 116 as illustrated in FIG. 3. Conditioned air 302 exiting the recirculating air handler 106, which may be filtered, heated, and humidified as needed is directed into the pan coater 102 through open valve 114 and prevented from entering the flow-through air handler 104 by closed valve 112. The exhaust air 304 is recirculated through the recirculating air handler 106 via the open valve 116 and prevented from entering the exhaust stack 126 by the closed valve 118.

The tablet coating system 100 may incorporate additional features to inhibit condensation of water from the airflow and/or to prevent any condensed water from entering the pan coater 102. In one aspect, one or more portions of the air ducts of the system 100 including, but not limited to, the supply duct 110 and/or the exhaust duct 108 of the pan coater 102, the inlet duct 124 or the exit duct 122 of the recirculating air handler 106, and any combination thereof may include insulation to reduce condensation resulting from heat losses within the ducts of the system 100. Any suitable insulation type may be selected to insulate the ducts of the tablet coating system 100 including, but not limited to insulating sheets, insulating wraps, foam insulation, and any other known insulation type.

In another aspect, the supply duct 110 and/or the exhaust duct 108 of the pan coater 102 may be installed in an orientation in which the ducts slope away from the pan coater 102 to inhibit the incursion of moisture formed within these ducts. In this aspect, any water condensation formed within each duct would travel along the downward slope of each duct, which is arranged to be away from the pan coater 102 in this aspect. The amount of slope may be specified using any method or standard known in the art. In one aspect, the slope may be greater than about 0.25 inches of vertical height change for each linear foot of duct. In various other aspects, the slope may be greater than about 0.3 inches of vertical height change, greater than about 0.5 inches of vertical height change, greater than about 0.75 inches of vertical height change, greater than about 1 inch of vertical height change, greater than about 2 inches of vertical height change, greater than about 3 inches of vertical height change, greater than about 4 inches of vertical height change, greater than about 5 inches of vertical height change, and greater than about 6 inches of vertical height change.

The tablet coating system 100 as disclosed herein overcomes many limitations of existing tablet coating systems. Due to the integration of the recirculating air handler 106 with the existing ductwork and controllers of the existing tablet coating systems, the tablet coating system 100 as disclosed may conduct an expanded repertoire of process steps within the same equipment without need for transfer to additional devices. In particular, the tablet coating system 100 as disclosed may conduct processes requiring high humidity and elevated temperature conditions by redirecting airflow through the recirculating air handler 106 as described herein above.

I. Recirculating Air Handler

In various aspects, a preexisting tablet coating system may be modified by incorporating a recirculating air handler 106 to supply air at an elevated temperature and elevated humidity beyond the capabilities of existing tablet coating systems. The incorporation of the recirculating air handler 106 is accomplished without affecting the ability of the modified tablet coating system 100 to perform all of the functions of the preexisting tablet coating system. In various aspects described herein below, the modified tablet coating system 100 is capable of switching between two operational modes: a preexisting mode in which the system 100 may perform all functions of the preexisting tablet coating system and a humidification mode in which high humidity airflow is delivered to the pan coater 102, thereby expanding the range of conditions that may be maintained within the pan coater 102 by the system 100.

The tablet coating system 100 as disclosed is capable of maintaining high humidity conditions within the pan coater 102 without risk of unwanted condensation through the inclusion of additional design features associated with the recirculating air handler 106 as described in detail herein below. Further, the recirculating air handler 106 maintains a low pressure within the pan coater 102 relative to the surrounding atmosphere to prevent the release of any contents of the tablet coating system 100, which may include noxious or bioactive compounds.

In one aspect, the recirculating air handler 106 is capable of providing an airflow to the pan coater 102 that is maintained at a temperature ranging from about 50° c. to about 80° c. and at a relative humidity of up to about 90%, including 85%, 86%, 87%, 88%, 89%, 90%, 91%, 92%, 93%, and 94%. This relative humidity level is well above the capability of existing tablet coating systems. Typical existing tablet coating systems reduce the humidity within the pan coater element to avoid the formation of condensation and resulting degradation of tablet coating quality.

Figure 4:
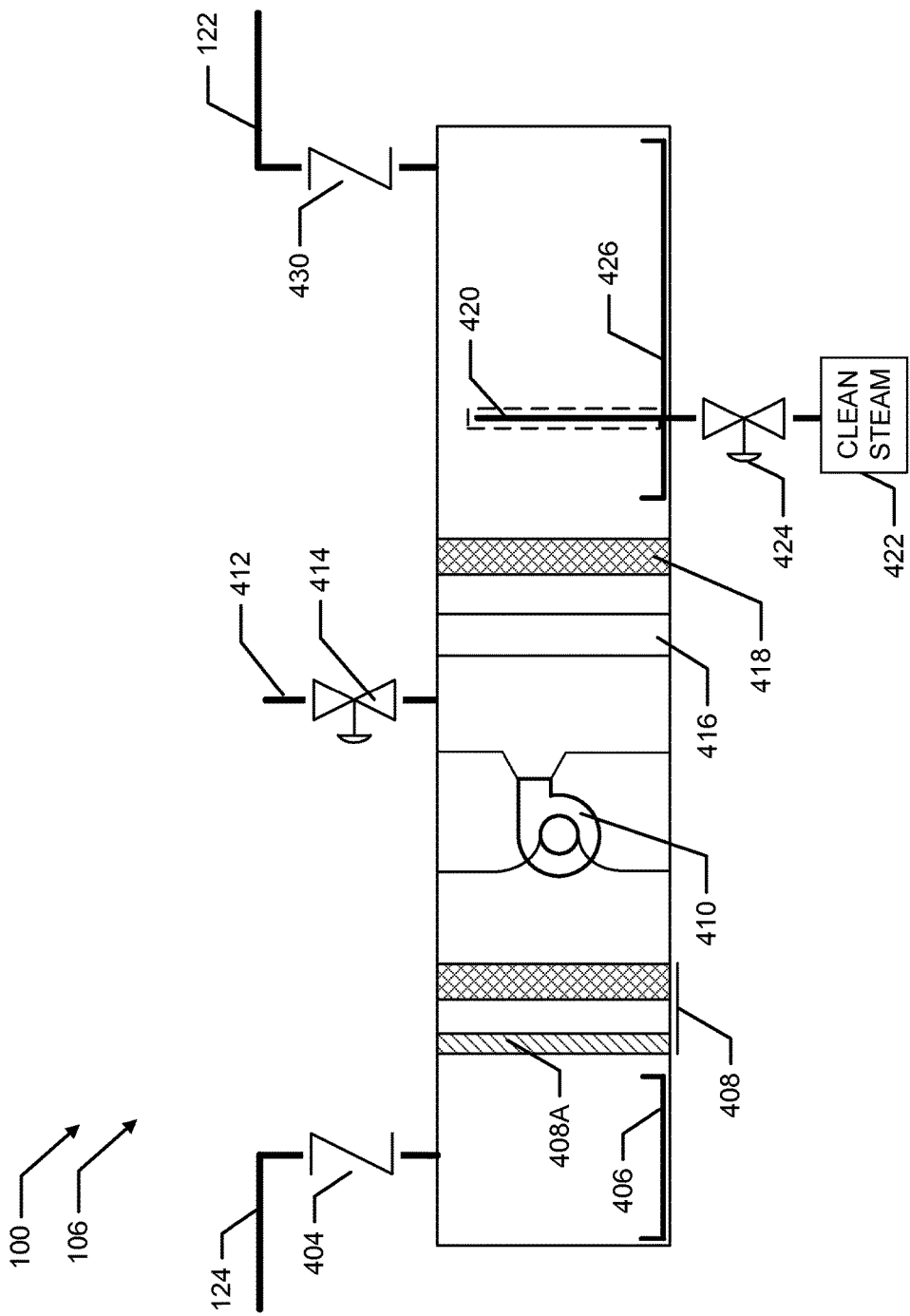
FIG. 4 is a block diagram illustrating the components of a recirculating air handler in an aspect.

FIG. 4 is a schematic diagram illustrating the arrangement of components of a recirculating air handler 106 in one aspect. The recirculating air handler 106 may receive exhaust air from the pan coater (not shown) via the inlet duct 124; the flow rate of the exhaust air into the recirculating air handler 106 may be modulated by adjusting the speed of the recirculation blower 410. The recirculating air handler 106 may include an inlet drain pan 406 to remove any condensation that may occur in this region as a result of condensation of the clean steam expanding through a vaporizer unit of the humidifier 420.

The recirculating air handler 106 may further include one or more inlet filters 408 to screen out any particulate matter within the airflow. Any filters known in the art may be selected for use as the one or more inlet filters 408 without limitation. The one or more inlet filters 408 may be selected based on any one or more factors including, but not limited to: size distribution of particles to be removed from airflow and the acceptable degree of impedance of flow imparted by the one or more inlet filters 408. In one aspect, the one or more inlet filters 408 may include a prefilter 408A to screen out the larger particles while passing the finer particles, and a second filter 408 to screen out the finer grains, as illustrated in FIG. 4. In various aspects, any known filter device may be used as the second filter 408 without limitation. Non-limiting examples of filters suitable for use as a second filter 408 include a HEPA filter and an ULPA filter.

The recirculating air handler 106 may further include an air blower 410 to accelerate the airflow in an amount sufficient to maintain the desired flow speed into the pan coater 102 as determined by sensor readings and control algorithms described herein below. Any known blower device may be selected for use as the air blower 410 without limitation. Non-limiting examples of suitable blower devices include axial flow fans and centrifugal fans. In an aspect, the speed of the air blower 410 may be continuously varied by increasing or decreasing an electrical parameter including, but not limited to, a supply voltage or a supply current.

Downstream of the air blower 410, the recirculating air handler 106 may further include a vent 412 connecting the airflow within the recirculating air handler 106 to the external atmosphere. The vent 412 may be controlled by a venting valve 414 which may opened in order to reduce pressure within the recirculating air handler 106 by an amount sufficient to maintain sub-atmospheric pressure within the tablet coating system 100 to prevent the escape of noxious or bioactive compounds from the system 100 during use. In an aspect, the venting valve 414 may be automatically actuated in response a control system command generated using measurements of pressure within the system 100 as described herein below.

The recirculating air handler 106 may further include a heater 416 situated downstream from the air blower 410 and vent 412. The heater 416 may increase the air temperature by an amount sufficient to maintain the desired air temperature within the pan coater 102. Any suitable type of air heater known in the art may be selected for use as the heater 416 without limitation including, but not limited to an electrical resistive heater. The output of the heater 416 may be modulated by a control system command generated using temperature measurements at one or more locations throughout the system 100 including, but not limited to: the exit of the recirculating air handler 106, the supply duct 110 of the pan coater 102, the exhaust duct 108 of the pan coater 102, and any other suitable location.

One or more exhaust filters 418 may be situated downstream of the air blower 410 and heater 416 to screen out any particulate matter within the airflow prior to humidification and delivery of the conditioned air to the pan coater 102. Any air filters known in the art may be selected for use as the one or more exhaust filters 418 without limitation. The one or more exhaust filters 418 may be selected based on any one or more factors including, but not limited to: size distribution of particles to be removed from airflow and the acceptable degree of impedance of flow imparted by the one or more exhaust filters 418. In one aspect, the one or more exhaust filters 418 may include a second HEPA or ULPA filter 418 as illustrated in FIG. 4.

A humidifier 420 may be situated within an exit region of the recirculating air handler 106 downstream of the one or more inlet filters 408, air blower 410, heater 416, and exhaust filter 418. The humidifier 420 may introduce clean steam into the airflow to increase the humidity within the airflow to a level sufficient to maintain the desired humidity within the pan coater 102, subject to one or more system constraints. In one aspect, the maximum humidity of the airflow downstream of the humidifier may be sufficiently low to prevent condensation within the pan coater 102 or the ductwork connecting the pan coater 102 with the recirculating air handler 106. In one aspect, the humidifier 420 may introduce an amount of humidity into the airflow to result in a relative humidity in the airflow of up to about 90%, including 85%, 86%, 87%, 88%, 89%, 90%, 91%, 92%, 93%, and 94%.

Any known humidifying device known in the art may be selected for use as the humidifier 420 including, but not limited to: an evaporative humidifier or a vaporizer. In one aspect, the humidifier 420 may be a vaporizer. In this aspect, the vaporizer may be provided with clean steam from a clean steam source 422 at a flow rate controlled by a steam valve 424. The steam valve 424 may be automatically opened and closed using a control signal generated using measured temperatures and humidities at one or more locations within the pan coater 102 and ducts of the tablet coating system 100.

To remove any condensed water resulting from the treatment of the airflow by the humidifier 420, the recirculating air handler 106 may further include a second drain pan 426 situated near the exit of the recirculating air handler 106. In one aspect, the second drain pan 426 may extend slightly upstream of the humidifier 420 as well as downstream of the humidifier 420, as illustrated in FIG. 4.

As illustrated in FIG. 4, the heated and humidified air may exit the recirculating air handler 106 via an exit duct 122 to be delivered to the supply duct connected to the pan coater 102.

II. Control System and Sensors

In various aspects, the modifications to a preexisting tablet coating system to produce the modified tablet coating system 100 of this disclosure may include one or more additional sensors to supplement the existing sensors associated with the unmodified tablet coating system at various locations throughout the system. The additional sensors may supplement the information obtained by the existing sensors, and information from all sensors may monitor the performance of the recirculating air handler 106 and may further provide feedback measurements used to modulate one or more processes associated with the operation of the recirculating air handler 106. Non-limiting examples of processes associated with the operation of the recirculating air handler 106 that may make use of the sensor measurements include: modulation of airflow exiting the vent 412; speed settings of the air blower 410; temperature settings of the heater 416; and steam valve settings for the humidifier 420.

Figure 6:
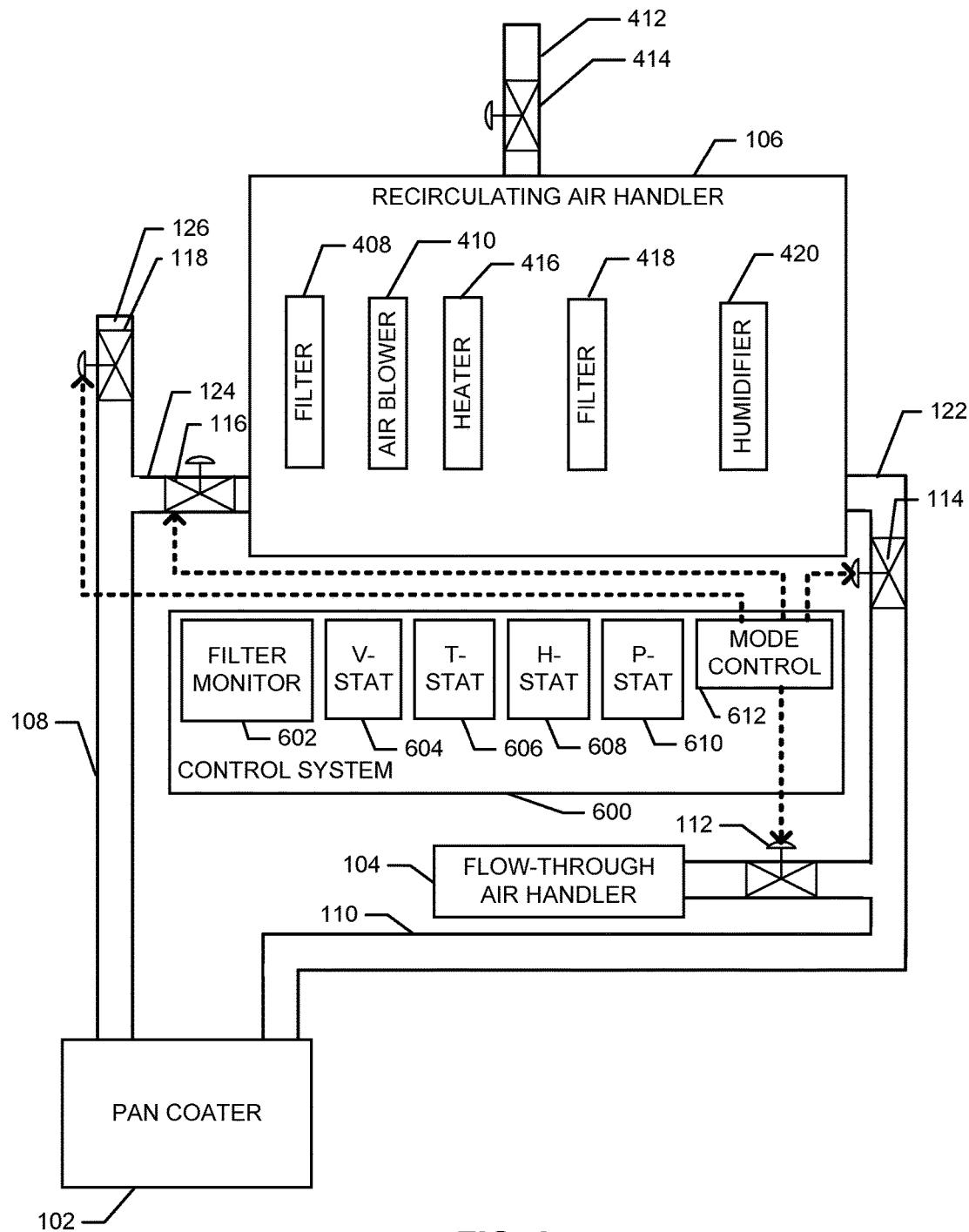
FIG. 6 is a block diagram illustrating the integration of the modules of a control system with the components of a tablet coating system, in particular the control of one or more valves of the system by the mode control module.

In an aspect, illustrated in FIG. 6, the modified tablet coating system 100 may further include a control system 600 to control the operation of various components and devices associated with the system 100. In one aspect, the control system 600 may automatically control the operation of one or more components and devices using feedback that may include measurements from one or more sensors situated at various locations within the system 100. As illustrated in FIG. 6, the control system 600 may include a mode control 612 to coordinate the opening and closing of valves to switch the air supply of the pan coater 102 from the flow-through air handler 104 to the recirculating air handler 106 as described herein previously. The control system 600 may further include a filter monitor 602 to monitor the operational status of the filters 408 and 418 within the recirculating air handler 106 and issue warnings to the system user when a filter is clogged and/or in need of cleaning or replacement. In addition, the control system 600 may further include a V-stat 604 to modulate the air flow within the system 100, a thermostat (T-stat) 606 to modulate the temperature within the system 100, an H-stat 608 to modulate the humidity within the system 100, and a P-stat 610 to modulate the pressure within the pan coater 102 of the system 100.

Figure 7:
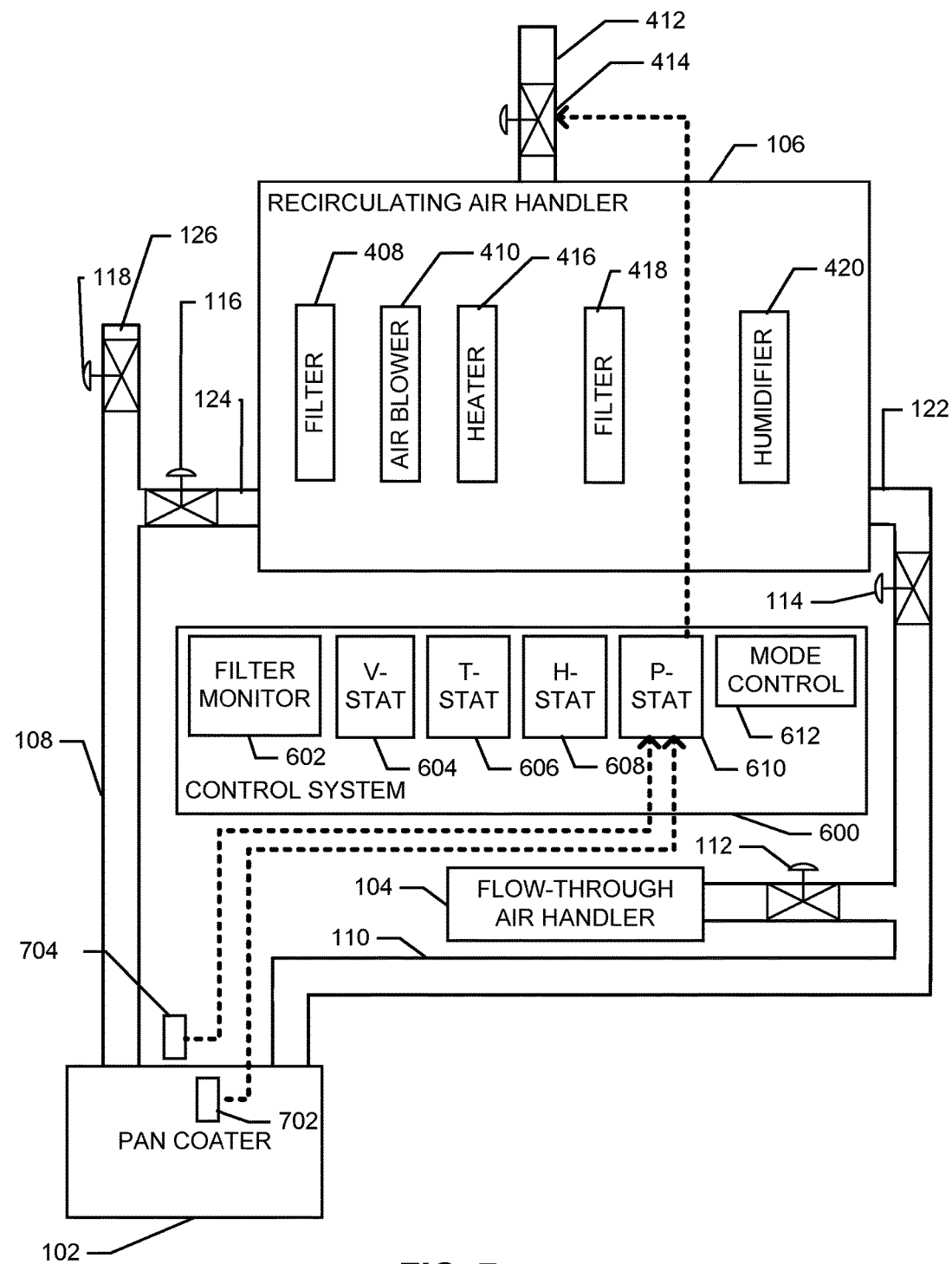
FIG. 7 is a block diagram illustrating the integration of the modules of a control system with the components of a tablet coating system, in particular the control of the venting valve by the P-stat module and associated pressure sensors.

Referring to FIG. 7, the mode control 612 may control the opening and closing of valves 112, 114, 116, and 118 to direct the airflow of the system 100 through the flow-through air handler 104 or the recirculating air handler 106 as needed. In this aspect, the mode control 612 may close valves 114 and 116 to cut off air flow through the recirculating air handler 106 and may open valves 112 and 118 to direct air flow through the flow-through air handler 104 and through the exhaust stack 126 to implement the preexisting mode of operation of the system 100. The model control 612 may alternatively close valves 114 and 116 to cut off flow-through air handler 104 and open valves 114 and 116 to direct air flow through the recirculating air handler 106 to implement a humidification mode of operation.

Pressure Sensors

In various aspects, pressure sensors may be incorporated at various locations throughout the tablet coating system 100 to monitor the operational status of various system components and to provide measurements used to modulate the operation of various system components. In particular, pressure measurements may be used by the control system to maintain the air pressure within the pan coater 102 at a sub-atmospheric pressure to minimize the release of contents of the pan coater 102 to the atmosphere.

Referring to FIG. 7, pressures may be measured by a first pressure sensor 702 situated on the interior of the pan coater 102 and a second pressure sensor 704 situated within the external atmosphere and used by the P-stat 610 to monitor the differential pressure to ensure that the pan coater pressure measured at sensor 702 is maintained below the atmospheric pressure measured at sensor 704 and to prevent the escape of any airflow from the pan coater 102, which may include noxious or bioactive compounds. In this aspect, if the differential pressure measurement indicates that the pressure within the pan coater 102 rises above a threshold pressure, the control system may command the venting valve 414 to open and relieve pressure within the system 100 until the differential pressure measurements indicate that the pressure measured at sensor 702 within the pan coater 102 has fallen back below a threshold pressure. In an aspect, the differential pressure measurements obtained by existing sensors may be integrated into the control system associated with the operation of the recirculating air handler 106. In another aspect, additional pressure sensors may be retrofitted to the pan coater 102.

The threshold pressure may be specified according to any criterion known in the art. In an aspect, the threshold pressure may be provided as a ratio of pressure within the pan coater 102 divided by the atmospheric pressure, wherein the ratio may range from about 0.95 to about 0.9995, including 0.95, 0.96, 0.97, 0.98, 0.99, 0.995, 0.999, and 0.9995. In another aspect, the threshold pressure may be provided as a difference in pressure calculated by subtracting the atmospheric pressure and the pressure inside the pan coater wherein the threshold pressure may be a minimum difference between the two pressures that may range from about 0.15 inches water column to about 0.3 inches water column, corresponding to pressure difference ranging from about 0.005 psig to about 0.01 psig. In various aspects, the minimum difference between the two pressures may be 0.15 inches water column, 0.175 inches water column, 0.2 inches water column, 0.225 inches water column, 0.25 inches water column, 0.275 inches water column, and 0.3 inches water column.

Figure 8:
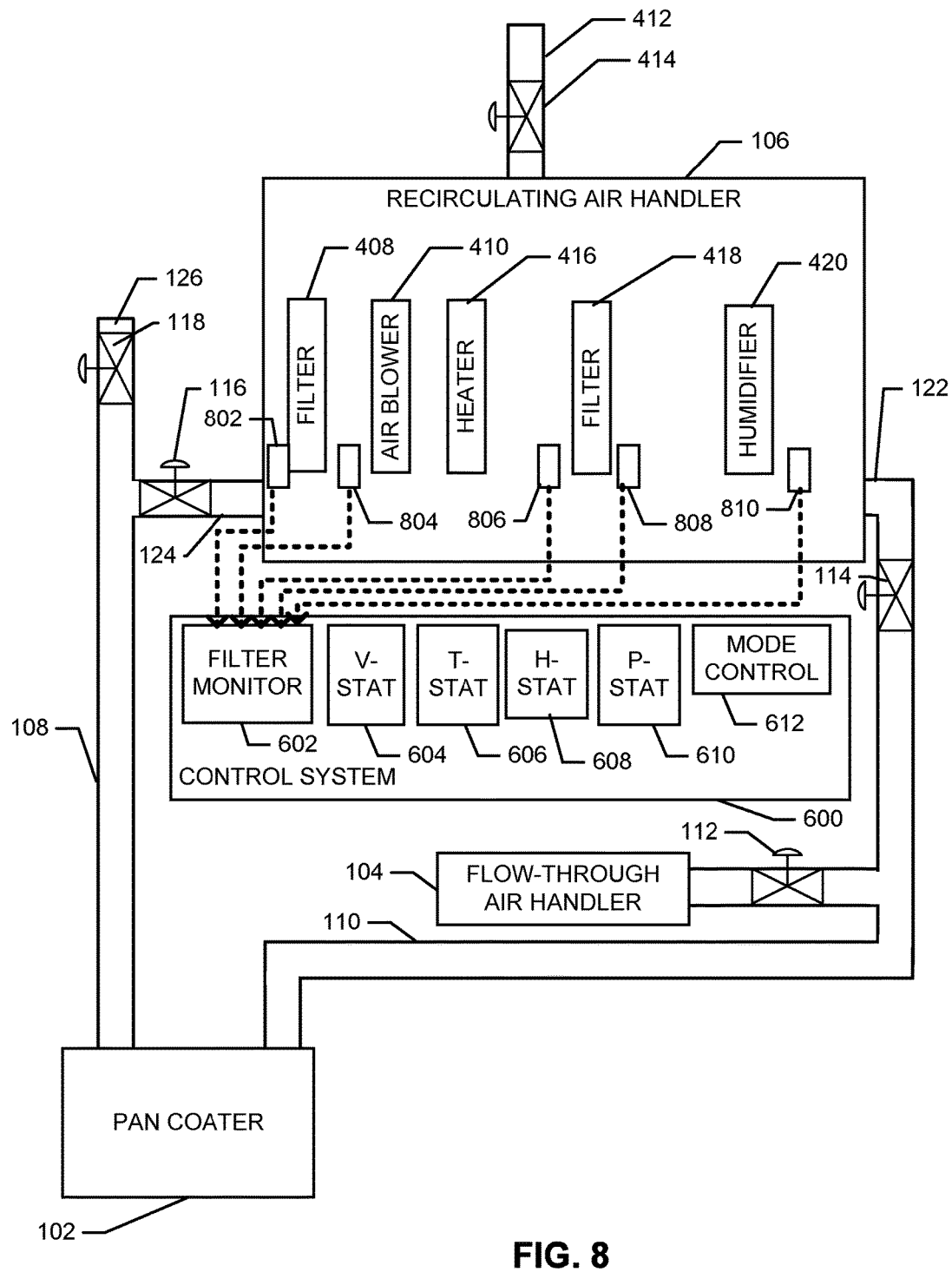
FIG. 8 is a block diagram illustrating the integration of the modules of a control system with the components of a tablet coating system, in particular the monitoring of filter conditions by the filter monitor module and associated pressure sensors.

In another aspect, shown in FIG. 8, the differential pressure between a region upstream and downstream of each filter within the recirculating air handler 106 may be monitored to assess the operational condition of the filter. As illustrated in FIG. 8, pressure sensors 802 and 804 may monitor the pressure upstream and downstream of a prefilter 408, respectively. Similarly, pressure sensors 806 and 808 may monitor the pressure upstream and downstream of a post-filter 418. Without being limited to any particular theory, as airborne particles accrue in a filter, the differential pressure upstream and downstream of the filter may increase due to increased flow blockage within the filter. If this differential pressure exceeds a threshold value, the control system 600 may issue an alert to inform an operator of the system 100 that the filter is fouled and in need of cleaning or replacement. The threshold value in this aspect may be influenced by at least one factor including but not limited to:

the size, thickness, and/or type of filter; the flow speed through the filter, and any other relevant factor known in the art.

In yet another aspect, the pressure within the exit of the recycling air handler 106 may be measured at pressure sensor 810 to monitor the operation of the recycling air handler 106 and tablet coating system 100. By way of non-limiting example, a sudden and significant rise in the measured exit pressure may indicate a blockage in one or more of the ducts or components of the tablet coating system 100.

Any appropriate pressure sensor known in the art may be selected for use as a pressure sensor in the tablet coating system 100. Non-limiting examples of suitable pressure sensors include: piezoresistive sensors, capacitive sensors, piezoelectric sensors, optical sensors, potentiometric sensors, and any other suitable sensor known in the art. In an aspect, the pressure sensor may additionally incorporate a switching mechanism for use with the control system to control the pressure within the pan coater 102 as described herein previously. In this aspect, the pressure sensor may further incorporate one or more user-definable set points connected to a switching mechanism.

By way of non-limiting example, the pressure sensor may incorporate a user-definable set point corresponding to the minimum allowable difference between the pan coater pressure and the atmosphere. In this example, if the pressure difference falls below this set point, the pressure sensor may activate a switching mechanism that generates a signal used by the control system to open the venting valve 414 of the recirculating air handler 106.

Temperature Sensors

In various aspects, temperature within the pan coater 102 represents a critical process condition in many tablet coating processes that may be subject to extensive monitoring and control by the tablet coating system 100. In processes conducted using heated and humidified air delivered by the recirculating air handler 106, the control of temperature throughout the system 100 operating in humidification mode as illustrated in FIG. 3 is critical to avoid condensation of water out of the air flow that may degrade tablet quality. Without being limited to any particular theory, if the temperature of the airflow falls below the dew point of the air, condensation of water is likely to occur. Dew point, as described herein, refers to the temperature at which the evaporation of water into the air and the condensation of water from the air occur at equal rates. Thus, the temperature of the air flow at various locations throughout the system 100 may be measured to confirm that air temperature is maintained above the dew point. In addition, temperature measurements may be used by the control system 600 to modulate the output of the heater 416 to increase or decrease the temperature of the air flow supplied by the recirculating air handler 106 as needed.

Figure 9:
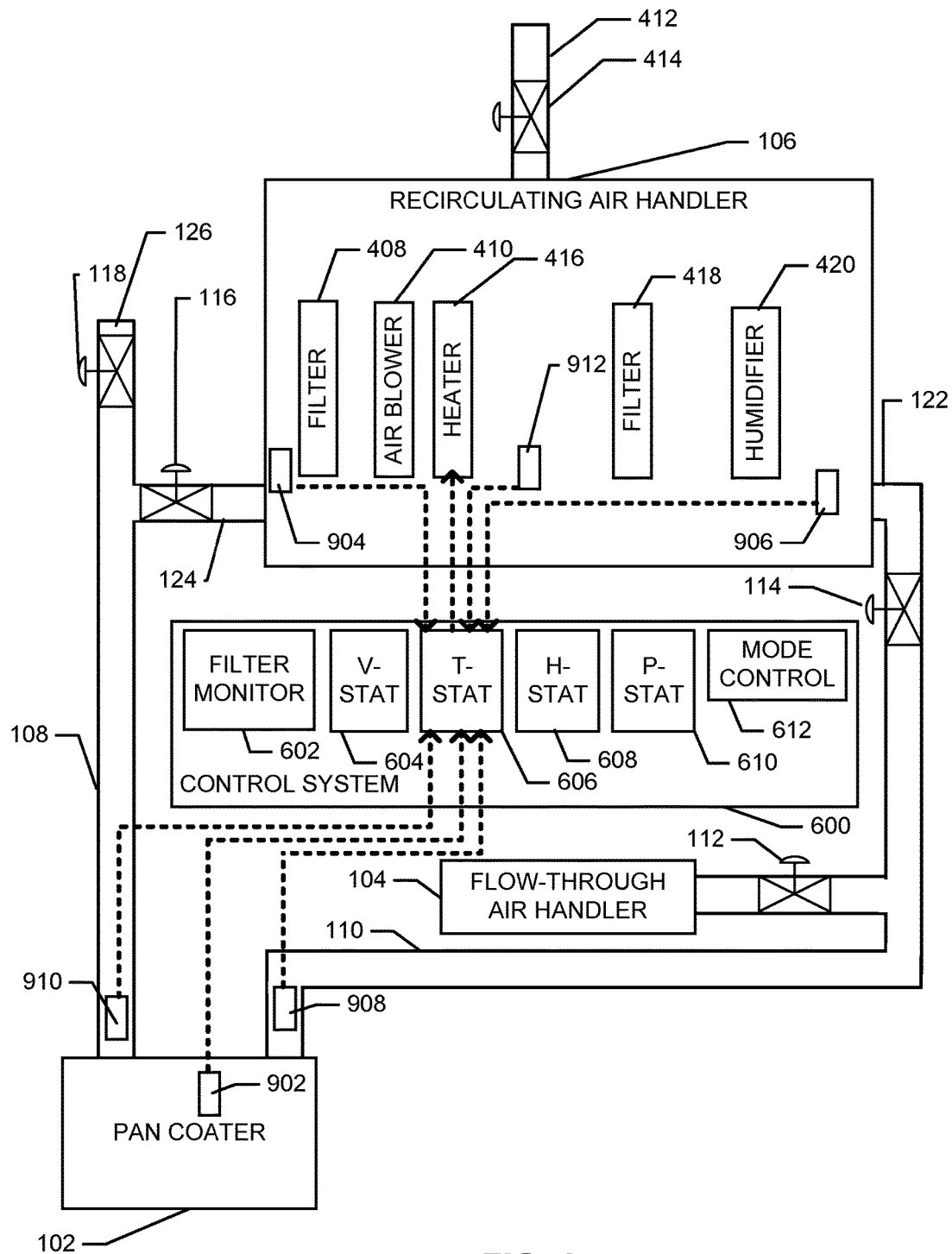
FIG. 9 is a block diagram illustrating the integration of the modules of a control system with the components of a tablet coating system, in particular the control of the air heater by the T-stat module and associated temperature sensors.

In various aspects, temperature sensors may be situated throughout the system 100 to monitor the air flow temperature. Referring to FIG. 9, in one aspect a temperature sensor 902 may be situated within the pan coater 102 to monitor the process conditions experienced by the tablets within the pan coater 102. In another aspect, temperature sensors 904 and 906 may be situated within the inlet and exit of the recirculating air handler 106, respectively, to monitor the temperature of the air entering and exiting the recirculating air handler 106.

In various other aspects, temperature sensors may be situated at one or more locations within the system 100 to provide measurements used to control the output of the heater 416 of the recirculating air handler 106. In one aspect, a temperature sensor 912 may be situated just downstream of the heater 416. In this aspect, if the temperature of the airflow measured at sensor 912 just downstream of the heater 416 exceeds a maximum temperature, the control system 600 may reduce the heat output of the heater 416. In this aspect, the maximum temperature may be selected based on at least one factor including, but not limited to, the heat resistance of materials and devices within the recirculating air handler 106 or a desired set point used to operate the tablet coating system 100. In one aspect, the maximum temperature may be a temperature set point used to modulate the output of the heater 416. In this aspect, the temperature set point may be specified by the system user and/or shifted upward or downward in order to achieve a desired temperature measured by the additional temperature sensor 902 within the pan coater 102.

In another aspect, a temperature sensor 908 may be situated within the supply duct 110 of the pan coater 102 to measure the supply air temperature and a second temperature sensor 910 may be situated within the exhaust duct 108 of the pan coater 102 to measure the discharge air temperature as an additional means of monitoring the air temperature within the pan coater 102 and the heat losses within the pan coater 102. The supply air temperature and/or the exhaust air temperature may also be used to modulate the amount of heat generated by the heater 416. In one non-limiting example, if the supply air temperature and/or exhaust air temperature for the pan coater 102 falls below a predetermined threshold temperature, the control system may command increased heat output by the heater 416 by shifting the temperature set point described herein above upward to a higher set point temperature. The predetermined threshold temperature may be selected based on at least one factor including, but not limited to: the desired temperature within the pan coater 102; the dew point of the air flow; and any combination thereof. In one aspect, the predetermined threshold temperature may be set to maintain the air temperature of the pan coater 102 at a temperature ranging from about 50° c. to about 70° c. as desired, including 45° c., 46° c., 47° c., 48° c., 49° c., 50° c., 51° c., 52° c., 53° c., 54° c., 55° c., 56° c., 57° c., 58° c., 59° c., 60° c., 61° c., 62° c., 63° c., 64° c., 65° c., 66° c., 67° c., 68° c., 69° c., 70° c., 71° c., 72° c., 73° c., and 74° c.

Humidity Sensors

Figure 10:
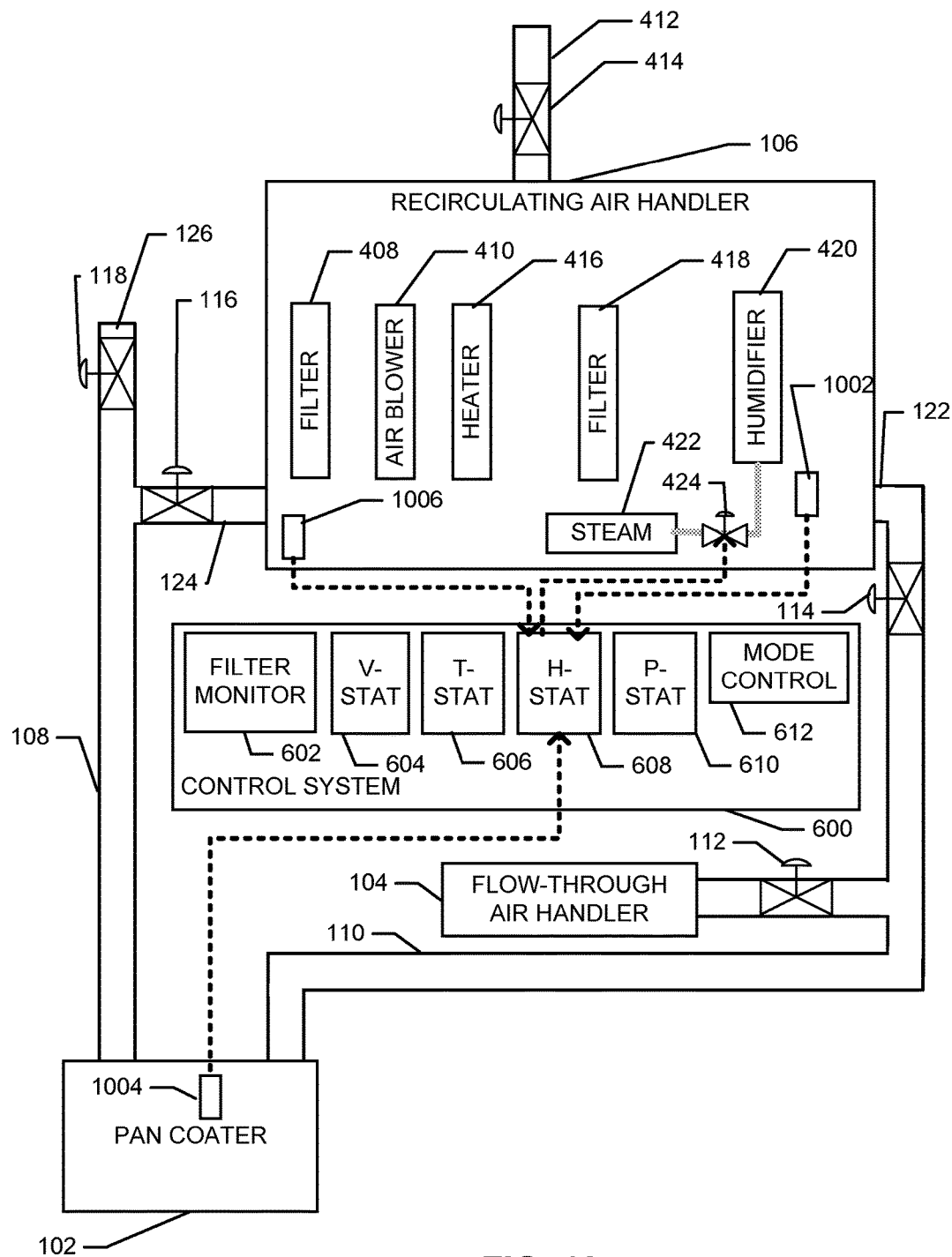
FIG. 10 is a block diagram illustrating the integration of the modules of a control system with the components of a tablet coating system, in particular the control of the air humidifier by the H-stat module and associated humidity sensors.

In various additional aspects, humidity sensors may be situated at various locations within the tablet coating system 100 to monitor the humidity within the airflow of the system. Non-limiting examples of suitable sensor locations, as illustrated in FIG. 10, include: a humidity sensor 1004 situated within the pan coater 102; a humidity sensor 1006 situated within the inlet of the recirculating air handler 106, and a humidity sensor 1002 situated within the exit of the recirculating air handler 106. In one aspect, the humidity measured by sensor 1002 at the exit of the recirculating air handler 106 may be used by the control system 600 to modulate the water vapor introduced by the humidifier 420.

Referring to FIG. 10, a humidity sensor 1002 situated at the exit of the recirculating air handler 106 may be used to modulate the amount of water vapor introduced by the humidifier 420. Typically, the control system 600 may open or close the steam valve 424 that controls the flow of clean steam from the clean steam source 422 in order to increase or decrease the humidity of the air flow as needed. In one aspect, a preselected humidity set point may be used to modulate the humidifier output. In this aspect, if the measured humidity is above or below a preselected humidity set point, or if the measured humidity falls outside a minimum and maximum humidity level defined within an error band of the desired humidity level, the control system 600 may increase or decrease the humidifier output as needed.

In another aspect, the humidity may be measured by an additional sensor 1004 situated within the pan coater 102. If the measured humidity at sensor 1004 exceeds a predetermined condensation threshold, the control system 600 may command the reduction of clean steam flow entering the humidifier 420 by closing the steam valve 424. The predetermined condensation threshold may be selected to be a humidity level at which condensation is likely to occur within the pan coater 102. In one aspect, the threshold level may be selected to maintain the dew point at least 10° c. below the temperature of the airflow. In various other aspects, the threshold level may be selected to maintain the dew point 10° c., 11° c., 12° c., 13° c., 14° c., 15° c., 16° c., 17° c., 18° c., 19° c., 20° c., 25° c., and 30° c. below the temperature of the airflow. In various other aspects, the threshold level may be selected to maintain the dew point at least 7° c., 8° c., 9° c., 10° c., 11° c., 12° c., 13° c., 14° c., 15° c., 16° c., 17° c., 18° c., 19° c., 20° c., 25° c., and 30° c. below the temperature of the airflow.

Without being limited to any particular theory, dew point depends on a combination of environmental conditions including, but not limited to, atmospheric pressure and moisture content of the air. Without being limited to any particular theory, at a constant pressure the dew point is proportional to the moisture content of the air. For example, an increase in humidity in the air corresponds to a higher dew point. The humidity measurement used by the control system 600 in this aspect may be obtained by the humidity sensors in terms of dew point or the control system 600 may calculate dew point based on measured humidity and atmospheric pressure using methods known in the art. In another aspect, if the dew point rises to within 5° c. below the temperature of the airflow, the control system 600 may completely shut down the humidifier output until the dew point falls to a level at which no risk of condensation within the pan coater 102 is likely. In various other aspects, the control system 600 may completely shut down the humidifier output if the dew point rises to within 0.5° c., within 1° c., within 2° c., within 3° c., within 4° c., within 5° c., within 6° c., within 7° c., within 8° c., within 9° c., within 10° c., within 15° c., or within 20° c. below the temperature of the airflow.

Air Flow Sensors

Figure 11:
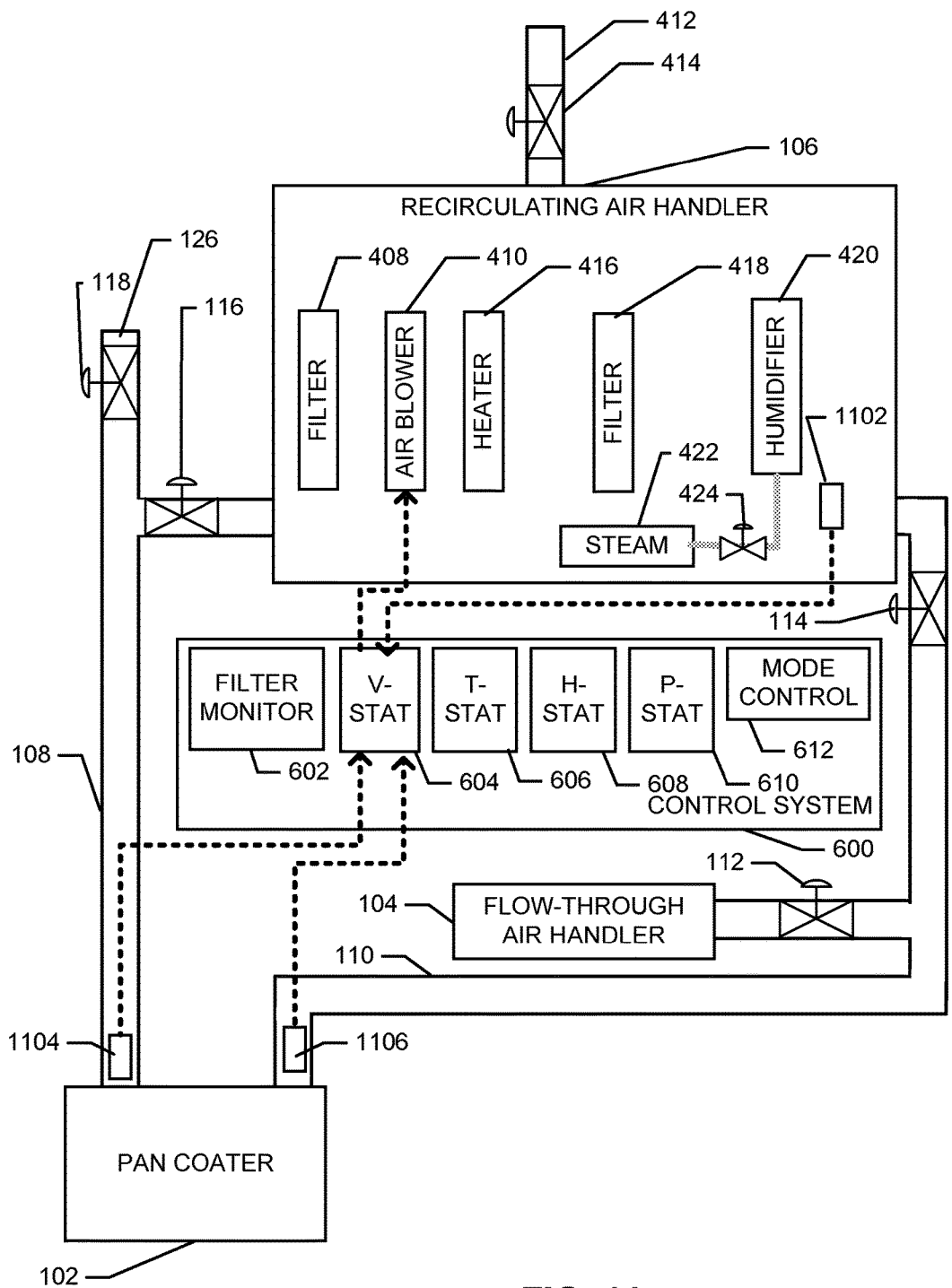
FIG. 11 is a block diagram illustrating the integration of the modules of a control system with the components of a tablet coating system, in particular the control of the air blower by the V-stat module and associated air flow sensors.

In various other additional aspects, air flow sensors may be situated at one or more locations within the tablet coating system 100 to monitor flow speed within the system 100. Referring to FIG. 11, in one aspect an air flow sensor 1102 may be situated within the exit of the recirculating air handler 106 and the air flow measurements may be used to modulate the output of the air blower 410 in order to achieve a desired air flow. Typically, the control system 600 may increase or decrease the power, current, and/or voltage supplied to the motor of the air blower 410 in order to increase or decrease the air flow as needed. In one aspect, a preselected air flow set point may be used to modulate the motor speed of the air blower 410. In this aspect, if the measured air flow is above or below a preselected air flow set point, or if the measured air flow falls outside a minimum and maximum air flow within an error band of the desired air flow level, the control system 600 may increase or decrease the air blower output as needed.

In another aspect, additional air flow sensors may be situated at other locations within the tablet coating system 100 to monitor air flow throughout the system 100. Non-limiting examples of additional air flow sensors include a sensor 1106 situated within the supply duct 110 and/or a sensor 1104 situated within the exhaust duct 108 of the pan coater 102.

III. Method of Generating High Humidity Conditions using Tablet Coating System

As described herein previously, the recirculating air handler 106 may be integrated into the preexisting components of the preexisting tablet coating system so as to retain full functionality of the preexisting tablet coating system. Typically, the preexisting tablet coating system directs airflow through the flow-through air handler 104 in a preexisting mode. Thus, the modified tablet coating system 100 may operate in this preexisting mode to perform a variety of procedures associated with the production of coated tablets including preheating tablets, applying one or more coating compositions to the tablets, and drying the tablets. In this preexisting mode, the temperature within the pan coater 102 may be maintained at a temperature of about 70° c. or above, including 70° c., 72° c., 74° c., 76° c., 78° c., 80° c., 85° c., 90° c., 100° c., 120° c., 140° c., 160° c., 180° c., and 200° c. Also in the preexisting mode, conditions within the pan coater 102 may be maintained at a dew point ranging from about 10° c. to about 15° c., including 10° c., 11° c., 12° c., 13° c., 14° c., and 15° c.

In various aspects, the tablet coating system 100 described herein previously may be operated in a humidification mode to provide humid process conditions within the pan coater 102 that are characterized by a temperature from about 50° c. to about 70° c., including 50° c., 52° c., 54° c., 56° c., 58° c., 60° c., 62° c., 64° c., 66° c., 68° c., and 70° c. In addition, process conditions in the humidification mode may be characterized by relatively high humidities corresponding to a dew point ranging from about 45° c. to about 70° c., and more specifically a dew point ranging from about 45° c. to about 55° c., including dew points of 45° c., 46° c., 47° c., 48° c., 49° c., 50° c., 52° c., 54° c., 56° c., 58° c., 60° c., 62° c., 64° c., 66° c., 68° c., and 70° c. In further aspects, the tablet coating system 100 described herein previously may be operated in a humidification mode to provide humid process conditions within the pan coater 102 that are characterized by relatively high humidities corresponding to a dew point within the range from about 45° c. to 50° c., 48° c. to 52° c., or 49° c. to 54° c. In even further aspects, the tablet coating system 100 described herein previously may be operated in a humidification mode to provide humid process conditions within the pan coater 102 that are characterized by relatively high humidities corresponding to a dew point within the range from about 48.5° c. to 49.5° c., 49.5° c. to 50.5° c., or 50.5° c. to 51.5° c. Optionally, the dew point in the humidification mode may be a constant dew point. The tablet coating system 100 and methods of the present invention described herein may provide the advantage of utilizing a higher constant dew point than the prior art, without condensation occurring. The ability to provide humid conditions as described herein without condensation occurring is significant because it prevents the tablets from dissolving or losing structural integrity. In one embodiment, lack of condensation may be established when the dew point is maintained at least at least 10° c. below the temperature of the airflow. Typically, these humid process conditions may be provided as one stage of a procedure carried out by the tablet coating system 100 to produce a batch of coated tablets. In one aspect, a method of providing humid process conditions may include establishing the air flow of the tablet coating system 100 through the recirculating air handler 106, introducing humidity into the airflow for a desired process duration, and subsequently redirecting the air flow of the system back through the flow-through air handler 104 to reconfigure the tablet coating system 100 back into the preexisting mode for subsequent process steps.

Figure 5:
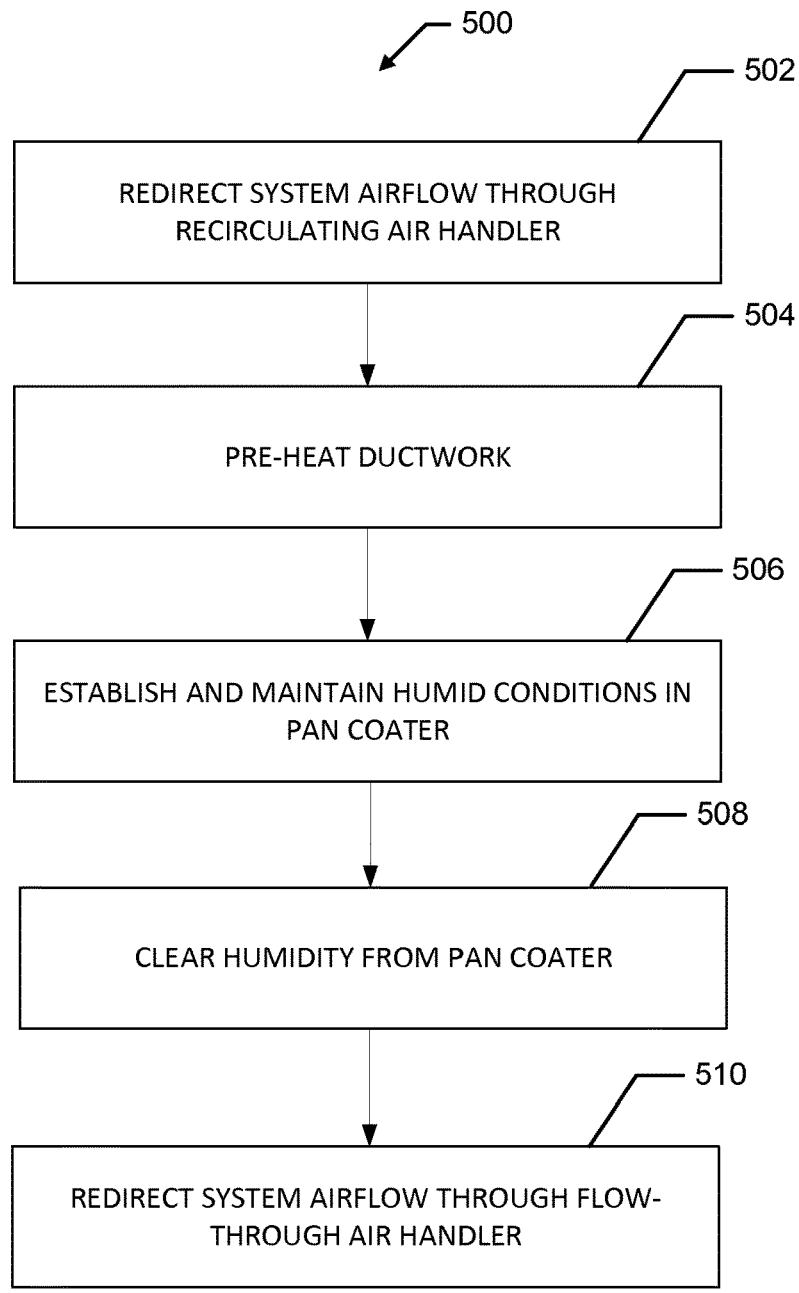
FIG. 5 is a flow chart illustrating the steps of a method to provide humid airflow to the pan coater of a tablet coating device as one stage of a tablet coating procedure in an aspect.

FIG. 5 is a flow chart illustrating a method 500 of providing humid process conditions within the tablet coating system 100 described herein above using the recirculating air handler 106. The method 500 includes configuring the tablet coating system 100 to direct airflow through the recirculating air handler 106 at step 502. In step 502, the airflow pattern is altered from the pattern illustrated in FIG. 2, in which the air flow passes through the flow-through air handler 104, to the pattern illustrated in FIG. 3, in which the air flow passes through the recirculating air handler 106.

In an aspect, step 502 includes shutting down the airflow through the flow-through air handler 104. In this aspect, valve 112 may be closed to prevent the exit of air flow through the flow-through air handler 104 and valve 118 may be closed to prevent the flow of exhaust air out of the exhaust stack 126. In addition, the components of the flow-through air handler 104 may be deactivated to shut down the operation of the flow-through air handler 104. Non-limiting examples of components of the flow-through air handler 104 include an air blower, an air heater, and a dehumidifier.

The method 500 at step 502 further includes establishing the airflow through the recirculating air handler 106. In this aspect, valve 116 may be opened to allow exhaust air from the pan coater 102 to pass into the recirculating air handler 106. In addition, the valve 114 may be opened to allow air flow to exit the recirculating air handler 106 an pass into the pan coater 102. In addition, the air blower 410 and heater 416 of recirculating air handler 106 may be activated to establish the desired temperature and flow rate appropriate for the humidifying step to be conducted within the pan coater 102. At step 502 and all subsequent steps, the pressure within the pan coater 102 is maintained at pressure that is at least about 0.15 inches of water column below the atmospheric pressure as described herein above, including 0.15 inches of water column, 0.2 inches of water column, 0.25 inches of water column, 0.3 inches of water column, 0.35 inches of water column, 0.4 inches of water column, 0.45 inches of water column, 0.5 inches of water column, 0.75 inches of water column, and 1 inch of water column below the atmospheric pressure.

The method 500 may further include preheating the ductwork and pan coater 102 of the tablet coating system 100 at step 504. By preheating the ductwork prior to the introduction of additional humidity into the airflow, condensation of water from the airflow may be inhibited. In step 504, the heater 416 and air blower 410 of the recirculating air handler 106 may be operating with the humidifier 420 disabled until the ductwork and pan coater 102 of the system 100 are determined to be fully heated. In one aspect, measurements from temperature sensors situated throughout the system 100 may be monitored to assess the heating of the ductwork. For example, if the temperature measurements are determined to be stabilized at essential values, the ductwork may be determined to be heated. In another example, if the difference in measured temperature of the airflow within the supply duct 110 and exhaust duct 108 is determined to be less than a predetermined threshold, the ductwork may be determined to be heated. The humid conditions may be maintained within the pan coater 102 for the duration of the humidification phase of the tablet coating procedure as needed.

The method 500 may further include establishing the humid conditions within the pan coater 102 at step 506. In this step, the humidifier 420 of the recirculating air handler 106 may be activated by opening the steam valve 424. Initially, the humidity may be introduced slowly and ramped up to the desired value of humidity within the pan coater 102. The temperature and dew point within the pan coater 102 may be monitored and used to adjust the output of the humidifier 420 during use. In addition, temperature and dew point may be monitored at other locations within the system 100 including, but not limited to, the inlet 124 and exit 122 of the recirculating air handler 106 to assess the likelihood of condensation forming anywhere in within the system 100 during use.

In various aspects, the humid conditions within the pan coater 102 may be established and maintained at conditions that prevent condensation from occurring anywhere within the system 100 during use. In one aspect, condensation and also lack of condensation may be assessed by visual inspection of the ducts and devices of the system 100 including but not limited to: the pan coater 102, the supply duct 110, the exhaust duct 108, and the recirculating air handler 106. In another aspect, condensation may be inferred by the detection of an air temperature within any duct or device of the system 100 that is less than about 10° C. above the measured dew point at any location within the system 100, including less than 5° c., 6° c., 7° c., 8° c., 9° c., 10° c., 11° c., 12° c., 13° c., 14° c., and 15° c. above the measured dew point.

Typically, the humidity may be introduced in an amount that maintains the measured temperature at least about 10° c. above the measured dew point at any location within the system 100, including 10° c., 15° c., 20° c., 25° c., 30° c., 40° c., 50° c., 60° c., 80° c., and 100° c. above the measured dew point. In one aspect, a warning may be issued if the measured temperature is within about 10° c. of the measured dew point at any location within the system 100, including within 5° c., 6° c., 7° c., 8° c., 9° c., 10° c., 11° c., 12° c., 13° c., 15° c., and 15° c. of the measured dew point at any location within the system 100. In another aspect, the system 100 may shut down the humidifier 420 if the measured temperature is within about 5° c. of the measured dew point at any location within the system 100, including within 2.5° c., 3° c., 3.5 C, 4° c., 4.5° c., 5° c., 5.5° c., 6° c., 6.5° c., 7° c., and 7.5° c. of the measured dew point at any location within the system 100. The humid conditions may be maintained within the pan coater 102 for the duration of the humidification phase of the tablet coating procedure as needed.

Upon completion of the humidification phase, the method 100 may further include lowering the humidity within the pan coater 102 to end the humidification phase of the tablet coating procedure. To this end, the method 100 may further include clearing the humidity from the pan coater 102 at step 508. In this step, the humidifier 420 may be deactivated by fully closing the steam valve 424 while maintaining the air temperature and flow rate within the system 100. In addition, the pressure within the pan coater 102 may be lowered slightly and maintained at a pressure of about 0.5 inches of water column below atmospheric pressure to facilitate the removal of humidity from the airflow, including 0.1 inches of water column, 0.2 inches of water column, 0.3 inches of water column, 0.4 inches of water column, 0.5 inches of water column, 0.6 inches of water column, 0.7 inches of water column, 0.8 inches of water column, 0.9 inches of water column, and 1 inch of water column below atmospheric pressure. The humidity may be monitored at various locations within the system 100 to assess the amount of humidity remaining within the system 100. In one aspect, the humidity may be determined to be removed from the system 100 when the measured dew point falls below a threshold value that may be about 15° c., including 10° c., 11° c., 12° c., 13° c., 14° c., 15° c., 16° c., 17° c., 18° c., 19° c., and 20° c.

Once the humidity is cleared from the pan coater 102 and other components of the system 100, the method 100 may further include redirecting system airflow back through the flow-through air handler 104 at step 510. In this step the air blower 410 and heater 416 may be deactivated to fully shut down the recirculating air handler 106. In addition, valves 114 and 116 may be closed to prevent airflow from entering or exiting the recirculating air handler 106. In addition, valve 112 may be reopened to allow the delivery of air flow from the flow-through air handler 104 to the pan coater 102. Further, valve 118 may be opened to allow the exhaust from the pan coater 102 to vent through the exhaust stack 126. Upon completion of step 510, the tablet coating system 100 may function in the preexisting mode in a manner similar to the most existing tablet coating systems.

Having described the invention in detail, it will be apparent that modifications and variations are possible without departing from the scope of the invention defined in the appended claims. Those of skill in the art should, however, in light of the present disclosure, appreciate that many changes could be made in the specific embodiments that are disclosed and still obtain a like or similar result without departing from the spirit and scope of the invention, therefore all matter set forth herein is to be interpreted as illustrative and not in a limiting sense.

What is claimed is:

1. A tablet coating system comprising:
   a pan coater operable to apply one or more coatings to a tablet; and
   a recirculating air handler operable to supply high humidity air flow to the pan coater, the recirculating air handler comprising:
      an inlet duct operable to receive exhaust air from the pan coater;
      a humidifier to introduce moisture into the exhaust air in an amount resulting in an exit air having a relative humidity of up to about 90%;
      a vent operable to open to release air from the recirculating air handler to the atmosphere via a vent valve, wherein the vent valve is opened as needed to maintain the pressure within the pan coater to at least 0.15 inches of water column below atmospheric pressure; and
      an exit duct operable to deliver the exit air to the pan coater.

2. The tablet coating system of claim 1, wherein the recirculating air handler further comprises at least one inlet filter situated upstream of the humidifier to remove particulate matter from an airflow entering the recirculating air handler and at least one exit filter situated downstream of the of the humidifier to remove particulate matter from an airflow exiting the pan coater.

3. The tablet coating system of claim 1, wherein the recirculating air handler further comprises at least one drain pan, wherein the at least one drain pan comprises one or more of:
   an inlet drain pan situated upstream of the humidifier and at least one filter to remove any condensation formed out of the exhaust air delivered from the pan coater; and
   an outlet drain pan to remove any condensation formed out of the exit air to be delivered to the pan coater, wherein the outlet drain pan is situated downstream of the humidifier and a portion of the outlet drain pan extends upstream of the humidifier.

4. The tablet coating system of claim 1, wherein the recirculating air handler further comprises:
   a supply air duct comprising a supply end operatively connected to supply air to the pan coater and an exit end opposite to the supply end and operatively connected to the exit duct of the recirculating air handler; and an exhaust duct comprising an exhaust end operatively connected to receive exhaust from the pan coater and an inlet end opposite to the exhaust end and operatively connected to the inlet duct of the recirculating air handler.

5. A tablet coating system to apply one or more coatings to a tablet, the tablet coating system comprising:
   a pan coater operable to apply one or more coatings to the tablet;
   a recirculating air handler to supply a humid air flow to the pan coater, the recirculating air handler comprising:
      an inlet duct operable to receive exhaust air from the pan coater;
      a humidifier to introduce clean steam into the exhaust air in an amount resulting in an exit air having a relative humidity of up to about 90%;
      a vent to release air from the recirculating air handler to the atmosphere via a vent valve, wherein the vent valve is opened as needed to maintain an air pressure within the pan coater of at least 0.15 inches of water column below atmospheric pressure; and
      an exit duct operable to deliver the exit air to the pan coater;
   a flow-through air handler to supply a low humidity air flow to the pan coater; and
   one or more ducts and one or more configurable valves, wherein the one or more configurable valves may be configured to:
      cut off flow through the recirculating air handler and direct the air flow from the flow-through air handler to a supply duct of the pan coater and from an exhaust duct of the pan coater to an exhaust stack; or cut off flow from the flow-through air handler and direct the air flow from exit duct of the recirculating air handler to the supply duct of the pan coater and from the exhaust duct of the pan coater to the inlet duct of the flow-through air handler.

6. The system of claim 5, further comprising at least one inlet filter situated upstream of the humidifier to remove particulate matter from an airflow entering the recirculating air handler and at least one exit filter situated downstream of the of the humidifier to remove particulate matter from an airflow exiting the recirculating air handler.

7. The system of claim 5, further comprising at least one drain pan, wherein the at least one drain pan comprises one or more of: an inlet drain pan situated upstream of the humidifier and at least one filter to remove any condensation formed out of the exhaust air delivered from the pan coater; and
   an exit drain pan to remove any condensation formed out of the exit air to be delivered to the pan coater, wherein the exit drain pan is situated downstream of the humidifier and a portion of the exit drain pan extends upstream of the humidifier.

8. The system of claim 5, wherein the one or more ducts comprise:
   the supply duct comprising a supply end operatively connected to supply air to the pan coater and an exit end opposite to the supply end and operatively connected to the exit duct of the recirculating air handler;

an exhaust duct comprising an exhaust end operatively connected to receive exhaust from the pan coater and an inlet end opposite to the exhaust end and operatively connected to the inlet duct of the recirculating air handler; an exhaust stack operatively connected to the exhaust duct between the exhaust end and the inlet end at one end and venting to the atmosphere at an opposite end; and a second supply duct operatively connected at a first end to an exit end of the flow-through air handler and operatively connected at a second end to the supply duct between the supply end and the exit end.

9. The system of claim 8, wherein the one or more valves comprise:

a first valve situated within the supply duct near the exit end;

a second valve situated within the exhaust duct near the inlet end;

a third valve situated within the exhaust stack; and a fourth valve situated within the second supply duct.

10. A method of supplying a humid air flow to a pan coater of a tablet coating system, the method comprising:

providing the pan coater to apply one or more coatings to a tablet;

providing a recirculating air handler operably connected to the pan coater, the recirculating air handler comprising:

an inlet duct operable to receive exhaust air from the pan coater;

a humidifier to introduce clean steam into an air flow of the exhaust air to produce humid exit air;

a vent to release air from the recirculating air handler to the atmosphere via a vent valve; and an exit duct operable to deliver the exit air to the pan coater;

establishing an air flow through the recirculating air handler operatively connected to receive exhaust air flow from the pan coater and to deliver a supply air flow to the pan coater;

heating the air flow to pre-heat the pan coater, a supply duct delivering air flow to the pan coater from the exit duct, and an exhaust duct receiving the exhaust air from the pan coater and delivering the exhaust air to the inlet duct;

establishing and maintaining a humid air flow within the pan coater for a duration of a humidification process, wherein the humid air is maintained at a humidity of up to about 90% relative humidity, and wherein an air pressure of at least 0.15 inches of water column below atmospheric pressure is maintained within the pan coater by venting air flow from the recirculating air handler to the atmosphere as needed; and clearing the humid air flow from pan coater.

11. The method of claim 10, wherein the air flow is heated to a temperature ranging from about 50° C. to about 80° C. and a dew point ranging from about 45° C. to about 55° C.

12. The method of claim 10, wherein the humid air flow is cleared from the pan coater by deactivating the humidifier and maintaining a pressure within the pan coater that is at least 0.25 inches of water column below atmospheric pressure.

13. The method of claim 10, further comprising reestablishing air flow through a flow-through air handler operatively connected to the supply duct and configured to receive external air from the atmosphere, wherein reestablishing air flow through the flow-through air handler comprises closing a first and second valve operable to block flow entering and exiting the recirculating air handler, opening a third valve operable to direct air flow from the flow-through air handler into the supply duct, and directing the exhaust flow from the pan coater through an exhaust stack into the atmosphere.

14. The method of claim 10, wherein the humid air flow is provided to the pan coater with essentially no formation of condensation.

\* \* \* \* \*